US010590331B2

(12) United States Patent
Rojas et al.

(10) Patent No.: US 10,590,331 B2
(45) Date of Patent: Mar. 17, 2020

(54) MIXED DIMERS FROM ALPHA-OLEFIN SULFONIC ACIDS

(71) Applicant: STEPAN COMPANY, Northfield, IL (US)

(72) Inventors: E. Carolina Rojas, Highland Park, IL (US); Xue Min Dong, Lincolnshire, IL (US); Aaron Sanders, Chicago, IL (US); Gregory P. Dado, Chicago, IL (US)

(73) Assignee: STEPAN COMPANY, Northfield, IL (US)

( * ) Notice: Subject to any disclaimer, the term of this patent is extended or adjusted under 35 U.S.C. 154(b) by 177 days.

(21) Appl. No.: 15/750,026

(22) PCT Filed: Jul. 28, 2016

(86) PCT No.: PCT/US2016/044378
§ 371 (c)(1),
(2) Date: Feb. 2, 2018

(87) PCT Pub. No.: WO2017/023665
PCT Pub. Date: Feb. 9, 2017

(65) Prior Publication Data
US 2018/0223173 A1 Aug. 9, 2018

Related U.S. Application Data

(60) Provisional application No. 62/200,986, filed on Aug. 4, 2015.

(51) Int. Cl.
| | |
|---|---|
| *C09K 8/592* | (2006.01) |
| *C11D 1/14* | (2006.01) |
| *C11D 1/22* | (2006.01) |
| *C07C 303/20* | (2006.01) |
| *C07C 303/22* | (2006.01) |
| *C07C 309/04* | (2006.01) |
| *C07C 309/05* | (2006.01) |
| *C07C 309/10* | (2006.01) |
| *C07C 309/19* | (2006.01) |
| *C07C 309/24* | (2006.01) |
| *C09K 8/584* | (2006.01) |
| *E21B 43/24* | (2006.01) |
| *E21B 37/06* | (2006.01) |
| *E21B 41/02* | (2006.01) |

(52) U.S. Cl.
CPC ............ *C09K 8/592* (2013.01); *C07C 303/20* (2013.01); *C07C 303/22* (2013.01); *C07C 309/04* (2013.01); *C07C 309/05* (2013.01); *C07C 309/10* (2013.01); *C07C 309/19* (2013.01); *C07C 309/24* (2013.01); *C09K 8/584* (2013.01); *C11D 1/143* (2013.01); *C11D 1/22* (2013.01); *E21B 43/2408* (2013.01); *C07C 2601/14* (2017.05); *E21B 37/06* (2013.01); *E21B 41/02* (2013.01)

(58) Field of Classification Search
CPC . C07C 2601/14; C07C 303/20; C07C 303/22; C07C 309/04; C07C 309/05; C07C 309/10; C07C 309/19; C07C 309/24; C09K 5/584; C09K 8/592; C11D 1/143; C11D 1/22; E21B 37/06; E21B 41/02; E21B 43/2408
See application file for complete search history.

(56) References Cited

U.S. PATENT DOCUMENTS

| | | | | |
|---|---|---|---|---|
| 3,721,707 | A | * | 3/1973 | Straus .................. C07G 17/002 562/101 |
| 3,951,823 | A | * | 4/1976 | Straus ................. B01F 17/0057 507/102 |
| 3,953,338 | A | | 4/1976 | Straus et al. |
| 4,059,620 | A | | 11/1977 | Johnson et al. |
| 4,344,485 | A | | 8/1982 | Butler |
| 4,556,107 | A | | 12/1985 | Duerksen et al. |

(Continued)

FOREIGN PATENT DOCUMENTS

| | | |
|---|---|---|
| CA | 1304287 C | 6/1992 |
| CN | 85106805 A | 3/1987 |

(Continued)

OTHER PUBLICATIONS

PCT International Search Report and Written Opinion dated Oct. 17, 2016 from corresponding Application No. PCT/US2016/044378, 11 pages.

*Primary Examiner* — Alicia Bland
(74) *Attorney, Agent, or Firm* — Dilworth IP, LLC

(57) ABSTRACT

Mixed dimer and mixed oligomer compositions are disclosed. The mixed dimer compositions comprise a monosulfonated cross-dimer or a salt thereof. The monosulfonated cross-dimer is a reaction product of (a) an alpha-olefin sulfonic acid (AOS acid); and (b) an unsulfonated olefin, an unsulfonated olefin precursor, or a functionalized olefin. The mixed oligomer compositions comprise a mono- or polysulfonated cross-oligomer or a salt thereof. The mono- or polysulfonated cross-oligomer is a reaction product of (a) an AOS acid; and (b) an unsulfonated diolefin or an unsulfonated diolefin precursor. Various methods for making the mixed dimer or oligomer compositions are described. Salts of the mixed dimer and oligomer compositions are useful surfactants for foams used in oilfield and other applications. The foams have improved high-temperature stability when compared with foams from AOS dimer acid salts.

20 Claims, No Drawings

(56) References Cited

U.S. PATENT DOCUMENTS

| | | | |
|---|---|---|---|
| 4,567,232 A | | 1/1986 | Echte et al. |
| 4,607,700 A | * | 8/1986 | Duerksen ............... C09K 8/592 166/303 |
| 4,813,483 A | | 3/1989 | Ziegler |
| 4,852,653 A | | 8/1989 | Borchardt |
| 4,957,646 A | | 9/1990 | Borchardt et al. |
| 5,052,487 A | | 10/1991 | Wall |
| 5,279,367 A | | 1/1994 | Osterloh |
| 6,043,391 A | | 3/2000 | Berger et al. |
| 2004/0242920 A1 | * | 12/2004 | Dado ................... C07C 303/22 562/41 |

FOREIGN PATENT DOCUMENTS

| | | |
|---|---|---|
| EP | 0446971 B1 | 7/1994 |
| GB | 2284601 A | 6/1995 |

\* cited by examiner

MIXED DIMERS FROM ALPHA-OLEFIN SULFONIC ACIDS

FIELD OF THE INVENTION

The invention relates to mixed dimers and oligomers from alpha-olefin sulfonic acids and methods for making them. Salts of these mixed dimer acids are useful surfactants for oilfield chemical and other applications.

BACKGROUND OF THE INVENTION

Oilfield chemical applications require robust surfactants that can provide good foaming at elevated temperatures and/or pressures. Suitable surfactants for this purpose include long-chain ($C_{16}$-$C_{18}$ or $C_{20}$-$C_{24}$) alpha-olefin sulfonates, alkyl aryl sulfonates, and salts of alpha-olefin sulfonic dimer acid ("AOS dimer acid," see, e.g., U.S. Pat. Nos. 4,556,107; 4,567,232; 4,607,700; 4,957,646; and U.S. Pat. No. 5,052,487). Dilute blends of alpha-olefin sulfonates and unsaturated fatty acids (e.g., oleic acid) have been used as steam foaming agents (see, e.g., U.S. Pat. No. 5,279,367).

Dimerization of alpha-olefin sulfonic acid ("AOS acid") is described, for example, in U.S. Pat. Nos. 3,721,707 and 3,951,823. Briefly, AOS acid produced by sulfonation of one or more alpha-olefins, is heated at 110° C. to 200° C. to induce oligomerization. Under these conditions, intermediate sultones and alkenesulfonic acids are converted to alkanesulfonic acids and other products. The molecular weight of the product is roughly double that of the AOS acid, and hence the term "AOS dimer acid" to describe it. However, the structure of the product can be rather complex, as illustrated in the '707 patent.

AOS dimer acid salts and other known alternative foamers were designed for use at temperatures commonly used for steam flooding, typically 160° C. to 180° C., while other oil recovery processes require foamers that can withstand even higher temperatures and pressures. One such process is steam-assisted gravity drainage ("SAGD"), which uses gravity to cause bitumen present in tar sands or other heavy oil deposits to melt and flow to a production well (see, e.g., U.S. Pat. No. 4,344,485 and Can. Pat. No. 1,304,287). SAGD applications may benefit from foamers that can perform well and resist thermal degradation at temperatures in the 210° C. to 250° C. range. So far, there are few suitable options, although AOS dimer acid salts are among the best known foamers for this purpose.

The oilfield chemicals industry would benefit from the availability of surfactants that can provide good foaming performance and thermal stability at the high temperatures and pressures utilized in SAGD and other oil recovery processes. Ideally, the surfactants would be straightforward to produce using conventional equipment and techniques and would provide improved high-temperature performance when compared with AOS dimer acid salts.

SUMMARY OF THE INVENTION

In one aspect, the invention relates to a mixed dimer composition. The composition comprises a monosulfonated cross-dimer or a salt thereof. The monosulfonated cross-dimer is a reaction product of (a) an alpha-olefin sulfonic acid (AOS acid); and (b) an unsulfonated olefin, an unsulfonated olefin precursor, or a functionalized olefin.

In another aspect, a mixed oligomer composition is provided. This composition comprises a mono- or polysulfonated cross-oligomer or a salt thereof. The mono- or polysulfonated cross-oligomer is a reaction product of (a) an AOS acid; and (b) an unsulfonated diolefin or an unsulfonated diolefin precursor.

In other aspects, the invention includes foams useful for oilfield and other applications, particularly high-temperature applications. The foams are produced by combining water, a gas, and a surfactant comprising the mixed dimer or mixed oligomer compositions described above.

In other aspects, the invention includes various methods used to make the mixed dimer or oligomer compositions. Some of the methods may provide mixed dimer or oligomer compositions having reduced levels of elemental sulfur compared with benchmark methods.

In yet another aspect, the invention includes a method for recovering oil from a subterranean reservoir formation. The method comprises injecting into the formation a mixed dimer or oligomer composition or a foam as described above, and then recovering oil from a production well.

We surprisingly found that the inventive mixed dimer and mixed oligomer compositions provide foams with improved high-temperature stability when compared with foams from AOS dimer acid salts. The mixed dimer and oligomer compositions can be made using methods similar to those now used to produce AOS dimer acids and their salts.

DETAILED DESCRIPTION OF THE INVENTION

The production of traditional alpha-olefin sulfonic dimer acid (AOS dimer acid) involves a self-dimerization reaction to give a nominally disulfonated molecule. In contrast, the inventive mixed dimer compositions comprise a substantial proportion of a monosulfonated material that may or may not have additional functionality.

I. Mixed Dimer Compositions

Mixed dimer compositions of the invention comprise a monosulfonated cross-dimer, or a salt thereof. The "cross-dimer" is an addition reaction product of (a) an alpha-olefin sulfonic acid (AOS acid); and (b) an unsulfonated olefin, an unsulfonated olefin precursor, or a functionalized olefin. In some aspects, at least one molar equivalent of the AOS acid is used. Because the same process that gives the cross-dimer also generates side products, including some AOS dimer acid and some dimers from the unsulfonated olefin, unsulfonated olefin precursor, or functionalized olefin, the "mixed dimer composition" may have multiple components that accompany the cross-dimer. For example, a mixed dimer composition produced by reacting 1-octene and a $C_{14}$-$C_{16}$ alpha-olefin sulfonic acid will contain the cross-dimer addition product of 1-octene and the $C_{14}$-$C_{16}$ AOS acid, but it will also contain some dimers (or oligomers) of 1-octene as well as some $C_{14}$-$C_{16}$ AOS dimer acid. In some instances, in addition to the dimers or oligomers mentioned above, the mixed dimer compositions may also contain some amount of undimerized starting material, i.e., some amount of unreacted AOS acid and/or some amount of unreacted unsulfonated olefin, precursor, or functionalized olefin.

A. The Alpha-Olefin Sulfonic Acid (AOS Acid)

The alpha-olefin sulfonic acid is prepared by sulfonation of an alpha-olefin. Suitable alpha-olefins have a $C_4$ to $C_{50}$ linear or branched carbon chain and a terminal carbon-carbon double bond. The alpha-olefins may comprise, for example, $C_8$ to $C_{40}$ alpha-olefins, $C_{10}$ to $C_{30}$ alpha-olefins, $C_{12}$ to $C_{18}$ alpha-olefins, $C_{14}$ to $C_{16}$ alpha-olefins, $C_{20}$ to $C_{24}$ alpha-olefins, $C_{26}$ to $C_{28}$ alpha-olefins, or combinations thereof.

Any method suitable for sulfonating alpha-olefins can be used to produce AOS acid useful for making the inventive compositions. In general, any method for converting alpha-olefins to hydroxyalkane sulfonic acids, sultones, alkene sulfonic acids, or mixtures thereof, may be used. Analysis of the crude sulfonic acid product normally shows the presence of 1,3- and 1,4-sultones, hydroxyalkane sulfonic acids, and alkene sulfonic acids. Thus, as used herein, "AOS acid" usually refers to a mixture of monomeric compounds, at least some of which have sulfonic acid functionality. Sulfonation with sulfur trioxide is preferred. For more examples of suitable alpha-olefin sulfonation processes, see U.S. Pat. Nos. 3,951,823; 4,556,107; 4,567,232; 4,607,700; and U.S. Pat. No. 4,957,646, the teachings of which are incorporated herein by reference.

Methods for sulfonating alpha-olefins with sulfur trioxide to generate alpha-olefin sulfonic acids are well known. One exemplary procedure is shown in U.S. Pat. No. 3,721,707, the teachings of which are incorporated herein by reference. Briefly, an alpha-olefin or mixture of alpha-olefins is introduced into a falling-film reactor along with a diluted mixture of sulfur trioxide and a diluent gas, which may be air or nitrogen, for example. A volatile solvent such as hexane or dioxane can be used as a diluent if desired. The reaction temperature is conveniently maintained within a desired range, for example, 40° C. to 70° C., by means of external cooling, and the product is kept cold.

As the skilled person will appreciate, the degree of sulfonation using $SO_3$ or other sulfonating agents might vary over a wide range depending on the desired outcome. Generally, the "degree of sulfonation" refers to the number of moles of sulfonating agent used per mole of alpha-olefin reactant. In some cases, it will be desirable to use a relatively high degree of sulfonation (e.g., 100-110%), while in other cases, it may be more desirable to use a relatively low degree of sulfonation (e.g., 20-95%).

B. Unsulfonated Olefin, Unsulfonated Olefin Precursor, or Functionalized Olefin.

For convenience, the unsulfonated olefin, unsulfonated olefin precursor, and functionalized olefin are sometimes referred to herein collectively as "the unsulfonated olefin reactants." The unsulfonated olefin can be any $C_3$ to $C_{50}$ linear, branched, or cyclic alpha-olefin or any $C_4$ to $C_{50}$ linear, branched, or cyclic internal olefin provided there is no sulfonic acid or sulfonate functionality. The unsulfonated olefin can be a pure compound or a mixture of different unsulfonated olefins. The unsulfonated olefins may comprise, for example, $C_8$ to $C_{40}$ alpha or internal olefins, $C_{10}$ to $C_{30}$ alpha or internal olefins, $C_{12}$ to $C_{18}$ alpha or internal olefins, $C_{14}$ to $C_{16}$ alpha or internal olefins, $C_{20}$ to $C_{24}$ alpha or internal olefins, $C_{26}$ to $C_{28}$ alpha or internal olefins, or combinations thereof. Suitable unsulfonated olefins include, for example, 1-hexene, 2-hexene, 3-hexene, 1-octene, 2-octene, 1-decene, 3-decene, 1-dodecene, 1-tetradecene, 1-hexadecene, 1-octadecene, cyclohexene, and the like, up to $C_{50}$ unsulfonated olefins. In some aspects, a linear alpha-olefin, particularly a $C_8$-$C_{20}$ linear alpha-olefin, is used. In other aspects, the unsulfonated olefin (or mixture) is the same as the olefin (or mixture) used to produce the AOS acid.

In some aspects, an unsulfonated olefin precursor can be used instead of the unsulfonated olefin. Thus, compositions that can form unsulfonated olefins under reasonably mild thermal conditions can be used to generate the unsulfonated olefin in situ. Suitable precursors include alcohols, alkyl halides, alkyl sulfates, and similar compositions that can undergo dehydration, dehydrohalogenation, or other elimination reactions to produce an unsulfonated olefin. Examples include 2-octanol, 3-decanol, 1-dodecanol, 1-tetradecanol, 1-hexadecanol, 2-decyl chloride, 1-dodecyl bromide, and the like. In some aspects, the unsulfonated olefin precursor is selected from saturated aliphatic $C_3$-$C_{50}$ alcohols and saturated aliphatic $C_3$-$C_{50}$ alkyl halides.

In other aspects, a functionalized olefin is included. The functionalized olefin can be used in place of or in combination with an unsulfonated olefin. Suitable functionalized olefins will have a carbon-carbon double bond and a functional group other than a sulfonate group. The functional group may be any functional group that is otherwise compatible with sulfonic acid groups and is stable under the dimerization reaction conditions. The functional group may be, for example, an amide, alcohol, phenol, carboxylic acid, carboxylate, ester, ether, ketone, nitrile, or other functional group. In some aspects, the functionalized olefin is an unsaturated fatty acid, such as oleic acid, or an unsaturated fatty alcohol, such as oleyl alcohol. As used herein, "functionalized olefin" also includes precursors to functionalized olefins, i.e., compounds that can provide a functionalized olefin upon dehydration, dehydrohalogenation, or other elimination reactions.

The relative amounts of the AOS acid and the unsulfonated olefin reactants can vary over a wide range and may depend on their relative reactivities, the reaction conditions, the equipment, the degree of conversion during the dimerization, the desired product composition, the intended end use, and other factors within the skilled person's discretion. Generally, the proportion of AOS acid will be 10 to 90 mole percent, 20 to 80 mole percent, 30 to 70 mole percent, or 40 to 60 mole percent based on the combined amounts of the AOS acid and the unsulfonated olefin reactants. In some cases, for example, it may be desirable to have a relatively large proportion of AOS dimer acid in the mixed dimer composition. In that case, the proportion of AOS acid to unsulfonated olefin reactant will be relatively high. When it is desirable to maximize the proportion of cross-dimer present, the proportion of unsulfonated olefin reactant might be significantly greater.

In some aspects, it may be desirable to minimize the amount of unsulfonated material in the mixed dimer composition. In that case, the mixed dimer composition can be extracted with a non-polar solvent such as petroleum ether to reduce the content of olefin dimers or oligomers. This process is referred to herein as "de-oiling," and the resulting treated mixed dimer compositions are referred to as "de-oiled" compositions. De-oiling can also be accomplished in some cases by stripping processes such as vacuum distillation or wiped-film evaporation. De-oiling might be desirable for making surfactants having greater sulfonic acid actives levels, as these compositions may provide salts having better foaming properties when used for oilfield or other applications (see, e.g., the results in Table 4 below).

The mixed dimer compositions may have sulfonic acid functionality, or some or all of the sulfonic acid groups may be in the form of salts following complete or partial neutralization. Any carboxylic acid groups present in the mixed dimer compositions may also be in either acid or salt form. Partial or complete conversion of the acidic product to the salt can be accomplished by neutralizing the acidic product with the desired amount of sodium hydroxide, potassium hydroxide, ammonium hydroxide, or the like. For use as a surfactant, at least some of the sulfonic acid groups, if not all of them, will be converted to salts, preferably alkali metal or ammonium salts, in the mixed dimer compositions.

In some aspects, wherein the unsulfonated olefin reactant is an unsulfonated olefin or an unsulfonated olefin precursor, the monosulfonated cross-dimer has a general structure selected from:

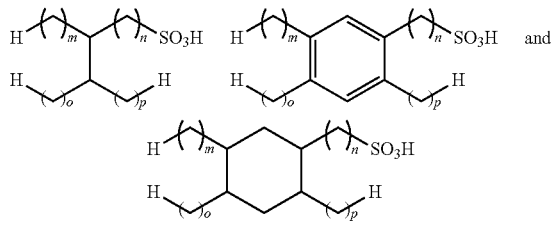

wherein m+n=3 to 49 and o+p=2 to 49 in the acyclic structure, and m+n=1 to 47 and o+p=0 to 47 in the cyclic structures, provided that the cross-dimer has at least 10 carbons. As the skilled person will appreciate, the structures given above are only a shorthand representation, as many isomers are possible and can be expected, including various possible substitution patterns within aromatic or other cyclic structures.

In some aspects, wherein the unsulfonated olefin reactant is a functionalized olefin, particularly an unsaturated fatty acid, the monosulfonated cross-dimer has a general structure selected from:

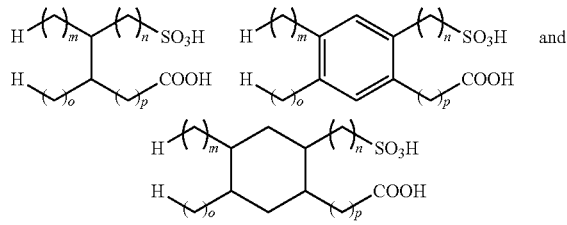

wherein m+n=3 to 49 and o+p=2 to 48 in the acyclic structure, and m+n=1 to 47 and o+p=0 to 46 in the cyclic structures, provided that the cross-dimer has at least 10 carbons. Again, as the skilled person will appreciate, the structures given above are only a shorthand representation, as many isomers are possible and can be expected, including various possible substitution patterns within aromatic or other cyclic structures.

Mixed dimer compositions can be made by heating a concentrated mixture comprising the AOS acid with the unsulfonated olefin, unsulfonated olefin precursor, or functionalized olefin at a temperature within the range of 110° C. to 200° C. for a time sufficient to produce the monosulfonated cross-dimer. Additional details of methods for preparing the compositions are included further below.

II. Mixed Oligomer Compositions

Mixed oligomer compositions of the invention comprise a mono- or polysulfonated cross-oligomer or a salt thereof. The cross-oligomer in this aspect is an addition reaction product of (a) an alpha-olefin sulfonic acid (AOS acid); and (b) an unsulfonated diolefin or an unsulfonated diolefin precursor. Because the same process that gives the desired cross-oligomer also generates side products, including some AOS dimer acid and some oligomers from the unsulfonated diolefin or unsulfonated diolefin precursor, the "mixed oligomer composition" may have multiple components that accompany the cross-oligomer. For example, a mixed oligomer composition produced by reacting a 1:2 molar mixture of 1,11-dodecadiene and a $C_{14}$-$C_{16}$ alpha-olefin sulfonic acid will contain the 1:2 cross-oligomer addition product of 1,11-dodecadiene and the $C_{14}$-$C_{16}$ AOS acid (i.e., a "cross-trimer"), but it may also contain some dimers or oligomers of 1,11-dodecadiene as well as some $C_{14}$-$C_{16}$ AOS dimer acid. In some instances, in addition to the dimers or oligomers mentioned above, the mixed oligomer compositions may also contain some amount of undimerized starting material, i.e., some amount of unreacted AOS acid and/or some amount of unreacted unsulfonated diolefin or unsulfonated diolefin precursor.

A. The Alpha-Olefin Sulfonic Acid

Suitable alpha-olefin sulfonic acids (AOS acid) for making the mixed oligomer compositions have already been described above in Section I.A.

B. Unsulfonated Diolefin or Unsulfonated Diolefin Precursor.

For convenience, the unsulfonated diolefin and unsulfonated diolefin precursor are sometimes referred to herein collectively as "the unsulfonated diolefin reactants."

The unsulfonated diolefin can be any $C_5$ to $C_{50}$ linear, branched, or cyclic alpha or internal diolefin provided there is no sulfonic acid or sulfonate functionality. The unsulfonated diolefin can be a pure compound or a mixture of different unsulfonated diolefins. The unsulfonated diolefins may comprise, for example, $C_8$ to $C_{40}$ alpha or internal diolefins, $C_{10}$ to $C_{30}$ alpha or internal diolefins, $C_{12}$ to $C_{18}$ alpha or internal diolefins, $C_{14}$ to $C_{16}$ alpha or internal diolefins, $C_{20}$ to $C_{24}$ alpha or internal diolefins, $C_{26}$ to $C_{28}$ alpha or internal diolefins, or combinations thereof. Suitable unsulfonated diolefins include, for example, 1,5-hexadiene, 2,5-hexadiene, 1,7-octadiene, 2,7-octadiene, 1,9-decadiene, 1,5-decadiene, 1,11-dodecadiene, 1,13-tetradecadiene, 1,15-hexadecadiene, 1,17-octadecadiene, and the like, up to $C_{50}$ unsulfonated diolefins.

In some aspects, an unsulfonated diolefin precursor can be used instead of the unsulfonated diolefin. Thus, compositions that can form unsulfonated diolefins under reasonably mild thermal conditions can be used to generate the unsulfonated diolefin in situ. Suitable precursors include diols, dihalides, disulfates, unsaturated alcohols, unsaturated alkyl halides, unsaturated alkyl sulfates, and similar compositions that can undergo dehydration or elimination reactions to produce an unsulfonated diolefin. Examples include 7-octen-2-ol, 9-decen-3-ol, 11-dodecen-1-ol, 13-tetradecen-1-ol, 15-hexadecen-1-ol, 9-chloro-1-decene, 11-bromo-1-dodecene, 1,8-octanediol, 1,14-tetradecanediol, and the like. In some aspects, the unsulfonated diolefin precursor is selected from $C_5$-$C_{50}$ diols, $C_5$-$C_{50}$ dihalides, monounsaturated aliphatic $C_5$-$C_{50}$ alcohols and monounsaturated aliphatic $C_5$-$C_{50}$ alkyl halides.

The relative amounts of the AOS acid and the unsulfonated diolefin reactants can vary over a wide range and may depend on their relative reactivities, the reaction conditions, the equipment, the degree of conversion during the oligomerization, the desired product composition, the intended end use, and other factors within the skilled person's discretion. Generally, the proportion of AOS acid will be 10 to 90 mole percent, 20 to 80 mole percent, 30 to 70 mole percent, or 40 to 60 mole percent based on the combined amounts of the AOS acid and the unsulfonated diolefin reactants. In some cases, for example, it may be desirable to have a relatively large proportion of AOS dimer acid in the mixed oligomer composition. In that case, the proportion of AOS acid to unsulfonated diolefin reactant will be relatively high. When it is desirable to maximize the proportion of cross-oligomer present, the proportion of unsulfonated diolefin reactant might be significantly greater.

As the skilled person will appreciate, the exact nature of the product mixture will depend on the proportion of AOS acid and unsulfonated diolefin reactants used. In some aspects, at least two molar equivalents of the AOS acid are reacted with the unsulfonated diolefin or unsulfonated diolefin precursor. In this case, the major addition reaction product will likely be a polysulfonated cross-oligomer. In other aspects, at least two molar equivalents of the unsulfonated diolefin or unsulfonated diolefin precursor are reacted with the AOS acid. In that case, the major addition reaction product will likely be a monosulfonated cross-oligomer.

In some aspects, it may be desirable to minimize the amount of unsulfonated material in the mixed oligomer composition. In that case, the mixed oligomer composition can be extracted with a non-polar solvent such as petroleum ether to reduce the content of unsulfonated olefin dimers or oligomers. De-oiling can also be accomplished in some cases by stripping processes such as vacuum distillation or wiped-film evaporation. As was discussed earlier, this process of "de-oiling" might be desirable for making surfactants having greater sulfonic acid actives levels, as these compositions may provide better foaming properties when used for oilfield or other applications.

The mixed oligomer compositions may have sulfonic acid functionality, or some or all of the sulfonic acid groups may be in the form of salts following complete or partial neutralization. Partial or complete conversion of the acidic product to the salt can be accomplished by neutralizing the acidic product with the desired amount of sodium hydroxide, potassium hydroxide, ammonium hydroxide, or the like. For use as a surfactant, at least some of the sulfonic acid groups, if not all of them, will be converted to salts, preferably alkali metal or ammonium salts, in the mixed oligomer compositions.

In some aspects, the AOS acid reacts with an unsaturated diolefin, an unsaturated alcohol, or some other unsulfonated diolefin precursor to give a polysulfonated cross-oligomer having the general structure:

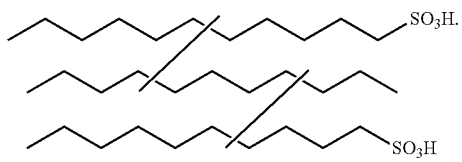

wherein any of the crosslinked fatty chains can have from 5 to 50 carbons.

This product might predominate in a reaction that uses a diol or an unsaturated alcohol when the reaction temperature is high enough to promote dehydration of the diol or unsaturated alcohol.

In some aspects, sultones present in the AOS acid may react with a diol or an unsaturated alcohol to give a polysulfonated cross-oligomer having the general structure:

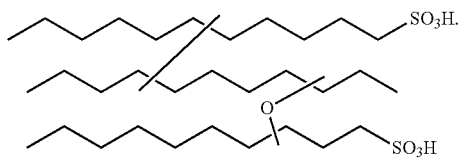

wherein any of the crosslinked fatty chains can have from 5 to 50 carbons.

The skilled person may be able to adjust the reaction conditions to favor either alcohol dehydration (and subsequent oligomerization) or ether formation. For instance, in some aspects, a relatively low reaction temperature might be used to produce an AOS acid having a relatively high sultone content. This AOS acid could provide mono- or polysulfonated cross-oligomers with relatively high ether content upon reaction of the AOS acid with a diol or an unsaturated alcohol.

Mixed oligomer compositions can be made by heating a concentrated mixture comprising the AOS acid with the unsulfonated diolefin or unsulfonated diolefin precursor at a temperature within the range of 110° C. to 200° C. for a time sufficient to produce cross-oligomers. More details regarding suitable methods for making both the mixed oligomer and mixed dimer compositions are provided below.

III. Methods of Making Mixed Dimer and Mixed Oligomer Compositions

The invention includes methods of making the mixed dimer and oligomer compositions. In some cases, the methods may provide a mixed dimer or oligomer composition having a reduced level of elemental sulfur when compared with other methods.

A. General Method

A general method for making mixed dimer and mixed oligomer compositions comprises two steps. First, an alpha-olefin is sulfonated, preferably with sulfur trioxide, to produce a mixture comprising an alpha-olefin sulfonic acid and sulfur dioxide. The mixture from the first step is then heated at a temperature within the range of 110° C. to 200° C. in a reactor with either (i) an unsulfonated olefin, an unsulfonated olefin precursor, or a functionalized olefin; or (ii) an unsulfonated diolefin or an unsulfonated diolefin precursor. The resulting product is, respectively, a mixed dimer or mixed oligomer composition of the invention. In other aspects, the heating is performed at 120° C. to 190° C., 130° C. to 170° C., or 140° C. to 160° C.

B. Alternate Method 1

In a first alternate method, the AOS acid and the unsulfonated olefin reactant (or unsulfonated diolefin reactant) are heated while purging sulfur dioxide and hydrogen sulfide from the reactor to produce the mixed dimer or oligomer composition. In some aspects, the resulting mixed dimer or oligomer composition has at least a 30% decrease in the level of elemental sulfur when compared with that of a mixed dimer or oligomer composition prepared by a similar process in the absence of any active removal of sulfur dioxide or hydrogen sulfide.

In Example 8, below, a mixed dimer composition from $C_{14}$-$C_{16}$ AOS acid and 1-tetradecene is produced while purging sulfur dioxide and hydrogen sulfide from the reactor. As shown in Table 3, the product has relatively low headspace $SO_2$ (<50 ppm) and $H_2S$ (3,000 ppm) at the end of the reaction, and the mixed dimer product has relatively low elemental sulfur (0.25 meq/g on a sulfonic acid basis).

In contrast, Example 7 shows the preparation of a mixed dimer from $C_{14}$-$C_{16}$ AOS acid and 1-tetradecene wherein the dimerization is performed in a closed reactor with no purging of sulfur dioxide or hydrogen sulfide. As shown in Table 2, the dimerized product contains a relatively high concentration of elemental sulfur (0.34 meq/g), and the reactor headspace at the conclusion of the dimerization contains higher concentrations of $SO_2$ (500 ppm) and $H_2S$ (>80,000 ppm).

Sulfur dioxide and/or hydrogen sulfide can be purged from the dimerization reactor by any suitable means. It is convenient, for instance, to sparge an inert gas such as nitrogen above and/or below the liquid surface in the reactor, and to recover the sulfur dioxide and/or hydrogen sulfide (hereinafter also called "oxidizables") in a scrubber containing aqueous base. Collecting the oxidizables in a scrubber enables quantification of these by-products by standard analytical methods, as is shown in Example 8.

Any desired flow rate for the sparge gas can be used, although there may be practical limits regarding the flow rate. A higher sparge rate may be more effective in eliminating sulfur dioxide and/or hydrogen sulfide, and it may provide a mixed dimer or oligomer having a relatively high sulfonic acid content. A desirable flow rate will depend on many factors, including the equipment involved, the mixing rate, the nature of the AOS acid and unsulfonated olefin or diolefin reactants, the viscosity of the mixed dimer or oligomer product, and other factors.

Sulfur dioxide and hydrogen sulfide could also be purged during the dimerization or oligomerization process by other methods. For instance, one could continuously or periodically introduce a solvent along with or instead of an inert gas. Vacuum could also be applied to assist in the purging of these by-product gases.

The degree of success in removing sulfur dioxide and/or hydrogen sulfide can be assessed using the analytical methods described herein as well as other techniques that will occur to the skilled person. In general, measuring the amounts of by-products (sulfur dioxide, hydrogen sulfide, elemental sulfur) present in the mixed dimer or oligomer composition, the amounts of off-gases (sulfur dioxide, hydrogen sulfide) collected in a scrubber, and the amount of sulfonic acid content in the mixed dimer or oligomer composition help to quantify the degree of success of the purging method.

C. Alternate Method 2

In another alternate method, sulfur dioxide is removed from the AOS acid prior to dimerization to produce a mixed dimer or mixed oligomer composition. In some aspects, the resulting mixed dimer or mixed oligomer composition will have a reduced level of elemental sulfur when compared with a product made by a similar method that does not include removal of sulfur dioxide from the AOS acid prior to dimerization or oligomerization.

Removal of sulfur dioxide can be performed by any desired method. Preferably, sulfur dioxide removal is performed by digesting, vacuum stripping, gas purging, solvent-assisted stripping, heating, or a combination thereof.

"Digesting" may refer to a soak period during which sulfur dioxide is allowed to evolve from a warm AOS acid product, or it may refer to a period during which the AOS acid is warmed or heated to promote sulfur dioxide evolution. In some aspects, a digestion step may precede or follow other sulfur dioxide removal methods.

When vacuum stripping is used, the amount of vacuum applied should be sufficient to remove sulfur dioxide from the reactor while also being insufficient to remove AOS acid or sultone intermediates from the reactor. The degree of vacuum that can be applied will depend on the molecular weight of the AOS acid, temperature, equipment, whether or not a solvent is included, whether or not a gas purge is used, and other factors within the skilled person's discretion. In some cases, it may be convenient to use a wiped-film evaporator for vacuum stripping. Wiped-film evaporation can be performed at relatively high temperatures (e.g., 130° C. or higher) with short residence times. This may allow removal of sulfur dioxide from the AOS acid without generating significant levels of hydrogen sulfide or elemental sulfur.

Gas purging can be used alone or in combination with other sulfur dioxide removal techniques. Air or inert gases such as nitrogen or argon can be used for purging. The purge should be performed under conditions sufficient to remove most or all of the sulfur dioxide present in the AOS acid prior to the dimerization or oligomerization step.

Solvent-assisted stripping can be used alone or in combination with gas purging and/or vacuum stripping. A volatile hydrocarbon solvent such as petroleum ether works well for this purpose.

Heating may accompany any of the earlier-described techniques, provided that the amount of heat is insufficient to induce a significant degree of dimerization or oligomerization. Typically, when heat is added, the temperature will be held within the range of 40° C. to 140° C., preferably 50° C. to 130° C.

For any of the sulfur dioxide removal methods or their combinations, the degree of success can be evaluated by measuring the amount of oxidizables (i.e., sulfur dioxide, hydrogen sulfide) present in a scrubbing device, solvent mixture, or other source of removed by-product gases using the analytical methods described below or other suitable analytical tools.

The invention includes salts made by neutralizing any of the mixed dimer or oligomer compositions mentioned above with an effective amount of a base, preferably an alkali metal hydroxide, alkaline earth metal hydroxide, ammonia, or an alkylammonium compound. The amount of base used will be sufficient to neutralize some or all of the sulfonic acid groups present in the mixed dimer or oligomer composition. The salts are useful surfactants for oilfield and other applications.

The salts may also be useful as surfactants for hard or soft surface cleaning, laundry detergents, personal care applications, enhanced oil recovery, oil dispersants, agricultural applications, emulsion polymers, metalworking, industrial applications, specialty foamers, and the like.

IV. Foams

The invention includes foams useful for oilfield and other applications. The foams comprise water, a gas, and a surfactant comprising the mixed dimer or oligomer compositions discussed above. In some aspects, the gas comprises steam, a non-condensable gas, or a mixture thereof. In some aspects, the non-condensable gas is air, nitrogen, carbon dioxide, natural gas, or a mixture thereof. In some aspects, the foam may have a foam quality within the range of 50% to 99%, or 60% to 95%, or 70% to 90%. "Foam quality" refers to the volume percentage of gas at a given temperature and pressure in the foam compared with the total volume of liquid and gas. Higher values are generally more desirable to minimize surfactant requirements. Thus, a foam made up of 70% nitrogen and 30% liquid would have a "foam quality" of 70%.

In some aspects, the foam may include other volatile organic compounds such as amines, alcohols, glycols, aminoalcohols, and the like, and mixtures thereof.

In other aspects, the foam may include foam boosters, co-surfactants, corrosion inhibitors, scale inhibitors, or other additives.

In still other aspects, the foam may include solid micro- or nanoparticles, which may have particle sizes in the range of 0.01 to 10 μm. Such micro- or nanoparticles may include, for example, carbon fibers, carbon nanotubes, colloidal silicas or other metal oxides, asphaltenes, or the like, or mixtures thereof.

We surprisingly found that foams generated from salts of the mixed dimer or mixed oligomer compositions, particularly de-oiled compositions, have improved high-temperature foam stability when compared with foams produced using AOS dimer acid salts. As used herein, "high temperature foam stability" means a reasonable resistance to foam dissipation at temperatures greater than 150° C., or within the range of 170° C. to 350° C., especially from 200° C. to 300° C. Several different screening tests were utilized, and the results were consistent: salts from the mixed dimer or oligomer compositions generally outperformed the corresponding $C_{14}$-$C_{16}$ AOS dimer acid salt, which may represent the state of the art for generating stable steam foams at high temperature.

The inventive foams can be utilized in a variety of oilfield or other applications for which foams having good high-temperature stability are desirable. Such processes might include, for example, steam flooding, cyclic steam stimulation, or steam-assisted gravity drainage ("SAGD").

Thus, in some aspects, the foams can be used to improve steam conformance in a SAGD process. In the SAGD process, closely spaced horizontal well pairs are drilled into oil sands deposits. Steam is injected, usually through one or more tubes or "stringers," into the upper ("injection") well. As the steam emerges from the stringer, it rises, heats the oil sands formation, softens the bitumen, and creates a widening steam chamber above the steam injection site. Heated bitumen flows by gravity and is drained continuously from the lower ("production") well. During start-up, there is a pressure difference between the injection and production wells, and this pressure difference helps to drive oil production. However, steam eventually breaks through to the production well and eliminates this pressure difference, and production becomes dominated by gravity flow rather than the combined effects of pressure and gravity. For examples of SAGD processes, see U.S. Pat. No. 4,344,485 and Can. Pat. No. 1,304,287, the teachings of which are incorporated herein by reference.

"Steam foam" refers to the product of combining steam with an aqueous mixture that contains a surfactant such that a foam is generated. In this case, the surfactant includes, as one component, a salt from a mixed dimer or mixed oligomer composition as described herein. When steam is converted to a steam foam, the steam's mobility is decreased such that heat from the steam is maintained for a prolonged time period in the bitumen-containing regions of the formation. Converting steam to steam foam helps to fully develop production of heavy oil. The steam foam may be produced above ground, but it is more commonly generated within a well. In some aspects, the steam foam is largely formed within the steam chamber. In some aspects, the steam foam may contain one or more non-condensable gases such as nitrogen or carbon dioxide. In other aspects, the steam foam may be present in the inter-well region between the injection and production wells. In other aspects, the steam foam may be generated in a water layer or gas cap that resides above the steam chamber. In some aspects, the steam foam or surfactant may be injected into a gas cap, the steam chamber, or other parts of the formation.

Thus, in one aspect, the invention relates to a method which comprises: (a) injecting into a subterranean reservoir formation, said formation comprising at least one injection well and at least one production well, a mixed dimer or oligomer composition or a foam made therefrom; and (b) recovering oil from the production well. In a preferred method, steam-assisted gravity drainage is used.

In an exemplary method of how to use the inventive steam foams for a SAGD application, a horizontal SAGD well pair comprising a steam injection well and a production well is provided. As is normal in a SAGD process, the injection well is located above the production well. A secondary well is created above the well pair. The secondary well can be substantially horizontal, substantially vertical, or angled with respect to the well pair. Preferably, the secondary well is horizontal and is substantially co-extensive with the SAGD well pair. The secondary well is preferably located near the top or just above the steam chamber of the injection well. Before, during, or after introduction of steam into the injection well, a surfactant solution comprising a salt of a mixed dimer or mixed oligomer composition of the invention is introduced into the secondary well. The surfactant solution can be introduced "slug-wise" in one or more portions, semi-continuously, or continuously into the secondary well. As the surfactant solution drains from the secondary well into a steam chamber of the injection well, it combines with rising steam to produce a steam foam in the injection well. As the steam foam expands, it fills some or all of the steam chamber and brings the steam foam into contact with portions of the steam chamber that would not be exposed to steam in the absence of the steam foam.

The following examples merely illustrate the invention; those skilled in the art will recognize many variations that are within the spirit of the invention and scope of the claims.

EXAMPLE 1

Preparation of a Mixed Dimer Composition from $C_{14}$-$C_{16}$ AOS Acid and 1-Octene AOS acid is prepared by falling-film sulfonation of a 65/35 (wt./wt.) mixture of 1-tetradecene and 1-hexadecene in accordance with standard manufacturing practices. The degree of sulfonation is 1.05 moles of $SO_3$ per mole of olefin, which corresponds to 3.62 meq $SO_3$ per gram of AOS acid and 3.46 meq olefin per gram of AOS acid.

The AOS acid (30.0 g, 0.104 mol olefin equivalent) is charged to a 100-mL round-bottom flask. 1-Octene (5.91 g, 0.053 mol) is added, and the mixture is stirred at 150° C. while maintaining a gentle nitrogen stream applied to the headspace of the reaction flask. After 6 h, $^1$H NMR analysis ($CDCl_3$) indicates full conversion as evidenced by a lack of detectable alkene and sultone signals. The mixed dimer product comprises 2.75 meq/g sulfonic acid as determined by titration with 0.1 N cyclohexylamine in methanol.

Neutralization of the product acid with NaOH in water to pH 10 affords sodium salts of the mixed dimer. A portion of the salt mixture is diluted with ethanol and then extracted with three portions of petroleum ether. The combined petroleum ether extracts are concentrated via rotary evaporation to afford an oil. The amount of extract is 8.4% by weight on a 100% sulfonic acid product basis. $^1$H NMR analysis of this oil indicates that the extract is non-sulfonated, saturated hydrocarbon that is consistent with the expected self-dimerization of 1-octene (dimerized olefin). Taking into account the amount of extract (2.3 wt. % based on sulfonic acid) that is typically observed when AOS dimer is prepared in the absence of added 1-octene, the amount of extract corresponds to about 40% of the amount of 1-octene used in the reaction. Therefore, the amount of 1-octene incorporated into the product as a cross-dimer with AOS acid is about 60% of the 1-octene charge.

EXAMPLE 2

Preparation of a Mixed Dimer Composition From $C_{14}$-$C_{16}$ AOS Acid and 1-Dodecene The procedure of Example 1 is used to prepare a mixed dimer composition comprising $C_{14}$-$C_{16}$ AOS acid and 1-dodecene. After 5 h of reaction at 150° C., $^1$H NMR analysis confirms complete dimerization/oligomerization as evidenced by the absence of alkene and sultone signals. Titration with cyclohexylamine indicates that the product comprises 2.46 meq/g of sulfonic acid.

EXAMPLE 3

Preparation of a Mixed Dimer Composition From $C_{14}$-$C_{16}$ AOS Acid and 1-Dodecanol A sample of $C_{14}/C_{16}$ AOS acid prepared as in Example 1 (50 g, 0.173 mol olefin equivalent) is charged a 100-mL round-bottom flask. 1-Dodecanol (16.4 g, 0.088 mol) is added, and the mixture is stirred at 150° C. while maintaining a gentle nitrogen stream applied to the headspace of the reaction flask. After 5 h, the reaction is checked for conversion by titration of an aliquot with 0.1 N cyclohexylamine in methanol. The sulfonic acid content is 0.81 meq/g, which is less than the sulfonic acid content of the reaction mixture prior to any heating (0.91 meq/g). This result indicates that dimerization has not proceeded to a significant extent, and that some conversion of alkene sulfonic acid to sultone has occurred. The reaction mixture is then heated to 170° C. for 2 h. Titration analysis indicates 2.39 meq/g sulfonic acid content. $^1$H NMR analysis confirms high conversion to dimerized product. Comparison of the $^1$H NMR spectrum to that of the product of Example 2 shows no significant difference in spectral characteristics between the products.

EXAMPLES 4-6

Preparation of a Mixed Dimer Composition From $C_{14}$-$C_{16}$ AOS Acid and 1-Hexadecene The procedure of Example 1 is used to prepare a mixed dimer composition comprising a $C_{14}$-$C_{16}$ AOS acid and 1-hexadecene at varying ratios as summarized in Table 1. In each example, $^1$H NMR analysis confirms complete dimerization/oligomerization as evidenced by the absence of alkene and sultone signals.

TABLE 1

Mixed Dimer Compositions from $C_{14}$-$C_{16}$ AOS Acid and 1-Hexadecene

| Ex. | $C_{14}$-$C_{16}$ AOS acid, g | 1-Hexadecene, g | Olefin:ACS acid[1] (mol/mol) | Reaction time, h | Sulfonic acid in product (meq/g) |
|---|---|---|---|---|---|
| 4 | 30.04 | 11.83 | 2:1 | 5.0 | 2.25 |
| 5 | 134.3 | 35.22 | 3:1 | 5.0 | 2.50 |
| 6 | 109.0 | 57.23 | 3:2 | 6.0 | 2.03 |

[1]AOS acid eq. wt. = 285 g/mol.

Analytical Methods Used for Examples 7-8
Headspace Analysis

Sulfur dioxide and hydrogen sulfide in reactor headspace is determined by means of Dräger gas analysis tubes. A single stroke with a handpump (Accuro, Drager Safety Inc.) is used to draw reaction headspace gas into the analysis tubes. For $H_2S$ analyses, 0.2%/A tubes are used, with an estimated lower detection limit of about 500 ppm. For $SO_2$ analyses, 50/b tubes are used, with an estimated lower detection limit of about 50 ppm.
Sulfonic Acid Content of Mixed Dimers Sulfonic acid content in the mixed dimer products is measured by potentiometric titration with 0.1 N cyclohexylamine in methanol.
Total Volatile Oxidizables Total volatile oxidizables stripped from reaction mixtures and captured by aqueous caustic scrubbing are quantified by the following titration method: A precise volume (typically 1.00 or 2.00 mL) of 0.1 N iodine solution is added to ~0.2 N aqueous HCl. Scrubber liquid (1.00 mL) is added. Excess unreacted iodine is titrated with 0.01 N sodium thiosulfate using a platinum electrode to determine the potentiometric endpoint. The oxidizables, which comprise $SO_2$ and $H_2S$, are calculated (in meq/g, mol/g) recognizing that 1 mole of $I_2$ reacts with 2 moles of sodium thiosulfate, 1 mole of $I_2$ reacts with 1 mole of $H_2S$, and 1 mole of 12 reacts with 1 mole of $SO_2$. The total meq/g of oxidizables is calculated based on the mass of scrubber liquid. The amount of oxidizables stripped is calculated based on the original mass of AOS acid charged to the reactor, expressed in meq/g. Oxidizables in sulfonic acid and neutralized reaction products are measured by a comparable iodine/thiosulfate titration method.
Sulfur Analysis Sulfur analyses (as elemental sulfur) are conducted by reaction of the sodium salts of reaction products, prepared by neutralization of sulfonic acid with NaOH in water, with a known amount of excess triphenylphosphine (TPP). The excess unreacted TPP is then titrated potentiometrically with iodine and the amount of elemental sulfur is calculated, based on the consumption of TPP and is reported in meq/g on a sulfonic acid basis.

EXAMPLE 7

Preparation of a Mixed Dimer Composition From $C_{14}$-$C_{16}$ AOS Acid and 1-Tetradecene (Closed Reactor)

A sample of the $C_{14}/C_{16}$ AOS acid prepared in Example 1 (112.5 g, 0.395 mol based on eq. wt.=285 g/mol) and 1-tetradecene (38.7 g, 0.197 mol) are charged to a 300-mL stainless-steel pressure reactor. The reactor is sealed and the stirrer is set to 350 rpm. The reactor contents are heated to 160° C. over 1 h, maintained for 5 h, and then allowed to cool to ambient temperature. $^1$H NMR analysis indicates high conversion as evidenced by the presence of only trace levels of alkene and sultone signals. Further analyses appear in Table 2.

TABLE 2

Mixed Dimer Composition from $C_{14}$-$C_{16}$ AOS Acid and 1-Tetradecene (Closed Reactor)

| | |
|---|---|
| Headspace $SO_2$ (ambient, end of reaction) | 500 ppm |
| Headspace $H_2S$ (ambient, end of reaction) | >80,000 ppm |
| Sulfonic acid in product | 2.15 meq/g |

TABLE 2-continued

Mixed Dimer Composition from $C_{14}$-$C_{16}$ AOS
Acid and 1-Tetradecene (Closed Reactor)

| | |
|---|---|
| Oxidizables in product (as $SO_2$ and/or $H_2S$) | 0.11 meq/g |
| Elemental sulfur (on a sulfonic acid product basis) | 0.34 meq/g |

As shown in Table 2, preparation of the mixed dimer composition without purging off-gases from the reactor headspace is accompanied by the generation of substantial amounts of $H_2S$ and elemental sulfur.

EXAMPLE 8

Preparation of a Mixed Dimer Composition From $C_{14}$-$C_{16}$ AOS Acid and 1-Tetradecene with Removal of $SO_2$ and $H_2S$ Throughout the Reaction A sample of the $C_{14}$/$C_{16}$ AOS acid prepared in Example 1 (112.5 g, 0.395 mol) and 1-tetradecene (38.7 g, 0.197 mol) are charged to a 300-mL stainless-steel pressure reactor equipped with a nitrogen sparge tube that directs gas to the impeller zone of a mechanical stirrer. The stirrer is set to 350 rpm, and then a nitrogen flow of 10 mL/min. is established. The gas exits through an outlet that feeds a scrubber containing 250 g of aqueous caustic (7 g of NaOH). The contents of the reactor are heated to 160° C. over 1 h and are then maintained for 5 h. The nitrogen flow is discontinued and the reactor contents are allowed to cool to ambient temperature. $^1$H NMR analysis indicates complete dimerization/oligomerization as evidenced by the absence of alkene and sultone signals. Further analyses appear in Table 3.

TABLE 3

Mixed Dimer Composition from $C_{14}$-$C_{16}$ AOS Acid and 1-Tetradecene (Removal of $SO_2$ and $H_2S$ Throughout the Reaction)

| | |
|---|---|
| Headspace $SO_2$ (ambient, end of reaction) | <50 ppm |
| Headspace $H_2S$ (ambient, end of reaction) | 3,000 ppm |
| Sulfonic acid in product | 2.28 meq/g |
| Oxidizables in product (as $SO_2$ and/or $H_2S$) | 0.03 meq/g |
| Elemental sulfur (on a sulfonic acid product basis) | 0.25 meq/g |
| Volatile oxidizables collected in scrubber (on starting reaction mixture weight basis) | 0.25 meq/g |

Compared with Example 7, the headspace reaction mixture comprises greatly reduced amounts of $SO_2$ and $H_2S$. In addition, the sulfonic acid content of the product is higher, which indicates a substantial reduction in the level of reduced sulfur compound generation. Measured oxidizables in the product are lower. Further, measured elemental sulfur in the sulfonic acid product is lower by 26% compared with that of the product of Example 7.

EXAMPLE 9

Preparation of a Mixed Dimer Composition From $C_{14}$-$C_{16}$ AOS Acid and Oleic Acid A sample of the $C_{14}$/$C_{16}$ AOS acid prepared in Example 1 (30 g, 0.104 mol olefin equivalent) is charged to a 100-mL round-bottom flask. Oleic acid (14.3 g, 0.053 mol, Palmac® 760, iodine value of 93.5, product of IOI Oleochemicals) is added, and the mixture is stirred at 150° C. for 28 h while maintaining a gentle nitrogen stream applied to the headspace of the reaction flask. $^1$H NMR analysis indicates high conversion to dimers/oligomers as evidenced by the presence of only trace levels of alkene and sultone signals. Titration of an aliquot with 0.14 N NaOH in a mixture of water and methanol shows two endpoints, interpreted as corresponding to sulfonic acid (1.99 meq/g) and carboxylic acid (0.22 meq/g). The carboxylic acid content corresponds to only about 19% of theory based on reaction charge, thereby indicating a significant degree of carboxylic ester and/or anhydride formation. The acid is neutralized in water with NaOH to afford a 10.4% solids, pH 10.2, turbid solution. Titration of an aliquot of this solution with 0.1 N HCl indicates a carboxylate content of 0.53 meq/g on a 100% solids basis, demonstrating that a significant liberation of carboxylate functionality occurs in the process of neutralization. Treatment of the neutralized solution with NaOH (0.60 meq/g on a 100% solids basis) and maintaining at 90° C. for 4 days results in a gradual increase in carboxylate content to 1.03 meq/g on a 100% solids basis, consistent with about 94% recovery of carboxylate functionality used in the original dimerization reaction charge.

EXAMPLE 10

Preparation of a Mixed Oligomer Composition From $C_{14}$-$C_{16}$ AOS Acid and Oleyl Alcohol A sample of the $C_{14}$/$C_{16}$ AOS acid prepared in Example 1 (198.8 g, 0.689 mol olefin equivalent) is charged a 1-L round-bottom flask equipped with overhead stirrer, nitrogen inlet, gas outlet, and thermocouple. Oleyl alcohol (93.48 g, 0.35 mol, HD Ocenol® 90/95 V, iodine value=94.8, hydroxyl value=208.5 mg KOH/g, product of BASF) is added. The mixture is stirred at 150° C. for 10.5 h while maintaining a 30 mL/min nitrogen stream applied to the headspace of the reaction flask. $^1$H NMR analysis indicates complete oligomerization as evidenced by the absence of alcohol, alkene, and sultone signals. Titration with cyclohexylamine indicates that the product comprises 2.11 meq/g of sulfonic acid. A sample of neutralized oligomer is then prepared by adding 150 g of sulfonic acid product to a solution of 12.7 g NaOH in 1337 g of water. The resulting opaque suspension (10% solids) has a pH of 11. Dilution of an aliquot of the suspension in water affords slightly hazy yellow solutions and demonstrates that the oligomer salts have substantial solubility in water at ambient temperature.

Foam Testing Performance of Mixed Dimer Compositions

Surfactant foaming properties at high temperature and high pressure are evaluated using a series of four test methods. Foam Test Methods 1-4 are screening methods that are performed using a 650-mL high-pressure Parr reactor having two pairs of observation windows on opposite sides of the reactor. The reactor is equipped with a heater, a port for pressurizing with nitrogen, mechanical stirring, and a glass liner, which has a capacity of 570 mL. The volume above the top window is about 250 mL, and the volume above the bottom window is about 450 mL. A light source is aimed from the back windows through the reactor toward the front windows so that the presence of foam or liquid is easily observed from the front windows.

Foam Test Method 1

A test solution or dispersion of 0.5 wt. % surfactant solids in deionized water is prepared, and 200 mL of the solution is introduced into the Parr reactor. The reactor is purged with nitrogen. The stirring speed is adjusted to 200-250 rpm, which is not expected to generate foam. The reactor contents are heated to a desired temperature (150° C., 200° C., or 250° C.) and the system is allowed to equilibrate at this temperature for 1 h. The stirrer is turned off, and the mixture is allowed to settle. Stirring is then started at maximum speed (about 1750 rpm) and continues for 3 min, generating foam. The stirrer is turned off, and a stopwatch is started. The upper window is observed until the foam level drops below it and light can be clearly seen through the window. The time noted is a measure of foam stability. The test is repeated three times for each sample and results are recorded.

Foam Test Method 2

A test solution or dispersion of 0.5 wt. % surfactant solids in sodium carbonate buffer is prepared. A sample (60 mL) is introduced into the Parr reactor, which is purged with nitrogen. The stirring speed is adjusted to 200-250 rpm, which is not expected to generate foam. The liquid level can be observed in the lower window. The reactor contents are heated to 250° C., and the system is allowed to equilibrate at this temperature for 1 h.

The stirring rate is increased to maximum speed (about 1750 rpm) for 1 min. Stirring is discontinued, and the stopwatch is started. Foam is observed through the lower window until the foam dissipates. The time, which is a measure of foam stability, is recorded. The test is repeated three times with 10-min. intervals of no stirring, and the average time for the foam to dissipate is recorded as foam stability.

Foam Test Method 3

A test solution or dispersion of 0.5 wt. % surfactant solids in deionized water is prepared. A sample (60 mL) is introduced into the Parr reactor, which is purged with nitrogen. The reactor is pressurized to 113 psig with nitrogen. The stirring speed is adjusted to 200-250 rpm, which is not expected to generate foam. The liquid level can be observed in the lower window. The reactor contents are heated to 250° C., and the system is allowed to equilibrate at this temperature for 1 h. Foam stability is then evaluated as described in Foam Test Method 2.

Foam Test Method 4

A test solution of 0.5 wt. % surfactant actives in deionized water is prepared. A sample (100 mL) is introduced into the Parr reactor, which is purged with nitrogen. The reactor is pressurized to 113 psig with nitrogen. The stirring speed is adjusted to 200-250 rpm, which is not expected to generate foam. The liquid level can be observed in the lower window. The reactor contents are heated to 250° C., and the system is allowed to equilibrate at this temperature for 1 h. Foam stability is evaluated as follows: The stirring rate is increased to maximum speed (about 1750 rpm) and continues for 15 min. Stirring is discontinued, and the stopwatch is started. Foam is observed through the lower window until the foam dissipates. The time, which is a measure of foam stability, is recorded. The experiments are done in duplicate.

Results from Foam Test Methods

Table 4 provides results from Foam Test Method 1 for a number of mixed dimer acid salt surfactant compositions. Some of the samples are used as produced. The "de-oiled" samples have had the unsulfonated olefin dimer portion removed by several extractions with petroleum ether. The control is a $C_{14}$-$C_{16}$ alpha-olefin sulfonic (AOS) dimer acid sodium salt (i.e., not a "mixed" dimer).

In general, the results show that foam stabilities are more difficult to maintain at 250° C. than at 200° C., although this can be counteracted somewhat with higher actives levels (1-2%). The de-oiled samples, which have a higher concentration of sulfonate groups, generally exhibit longer foam stabilities. Especially at 200° C., all of the de-oiled mixed dimer acid salt products outperform the $C_{14}$-$C_{16}$ AOS dimer acid sodium salt.

Table 5 provides results from Foam Test Method 2 for a number of mixed dimer acid salt surfactant compositions. Average foam stabilities are reported in the table. Again, the control is a $C_{14}$-$C_{16}$ AOS dimer acid sodium salt. All of the mixed dimer test samples provide foam stabilities that are as good as or better than the stabilities observed with the control.

Table 6 provides results from Foam Test Method 3. Average foam stabilities are reported in the table. The control is a $C_{14}$-$C_{16}$ AOS dimer acid sodium salt. All of the mixed dimer and mixed oligomer test samples provide improved foam stabilities (66-95% more stable) when compared with the stabilities obtained using the control.

Table 7 provides results from Foam Test Method 4. Average foam stabilities are reported in the table. The control is a $C_{14}$-$C_{16}$ AOS dimer acid sodium salt. Both the mixed dimer and mixed oligomer test samples provide improved foam stabilities when compared with the stabilities obtained using the control.

TABLE 4

Results from Foam Test Method 1

| Surfactant | Surfactant solids, wt. % | Ave. foam stability (s) 150° C. | 200° C. | 250° C. |
|---|---|---|---|---|
| $C_{14}$-$C_{16}$ AOS dimer Na salt (control) | 0.5 | 282 | 459 | 110 |
| 2:1 $C_{14}$-$C_{16}$ AOS/oleic acid mixed dimer Na salt | 0.5 | 469 | 530 | 108 |
| 2:1 $C_{14}$-$C_{16}$ AOS/oleic acid mixed dimer Na salt, de-oiled | 0.5 | 292 | 883 | 191 |
| 2:1 $C_{14}$-$C_{16}$ AOS/hexadecene mixed dimer Na salt | 0.5 | 314 | 422 | 78 |
| 2:1 $C_{14}$-$C_{16}$ AOS/hexadecene mixed dimer Na salt, de-oiled | 0.5 | 560 | 1522 | 165 |
| 2:1 $C_{14}$-$C_{16}$ AOS/dodecene mixed dimer Na salt | 0.5 | 389 | 643 | 87 |
| 2:1 $C_{14}$-$C_{16}$ AOS/dodecene mixed dimer Na salt, de-oiled | 0.5 | 301 | 684 | 126 |
| 2:1 $C_{14}$-$C_{16}$ AOS/dodecene mixed dimer Na salt, de-oiled, +2% KCl | 0.5 | 360 | 386 | 75 |
| 2:1 $C_{14}$-$C_{16}$ AOS/dodecene mixed dimer Na salt, de-oiled, +4% KCl | 0.5 | 241 | 388 | 60 |
| 2:1 $C_{14}$-$C_{16}$ AOS/dodecene mixed dimer Na salt, de-oiled | 1.0 | 579 | 556 | 223 |
| 2:1 $C_{14}$-$C_{16}$ AOS/dodecene mixed dimer Na salt, de-oiled | 2.0 | 602 | 402 | 147 |
| 2:1 $C_{14}$-$C_{16}$ AOS/octene mixed dimer Na salt | 0.5 | 415 | 732 | 20 |
| 2:1 $C_{14}$-$C_{16}$ AOS/octene mixed dimer Na salt, de-oiled | 0.5 | 488 | 798 | 59 |

TABLE 5

Results from Foam Test Method 2

| Surfactant | Surfactant solids, wt. % | $Na_2CO_3$ buffer, wt. % | Ave. foam stability (s) at 250° C. |
|---|---|---|---|
| $C_{14}$-$C_{16}$ AOS dimer Na salt (control) | 0.5 | 0.5 | 37 |
| 2:1 $C_{14}$-$C_{16}$ AOS/oleic acid mixed dimer Na salt | 0.5 | 0.5 | 39 |
| 2:1 $C_{14}$-$C_{16}$ AOS/hexadecene mixed dimer Na salt | 0.5 | 0.5 | 53 |

TABLE 5-continued

Results from Foam Test Method 2

| Surfactant | Surfactant solids, wt. % | Na₂CO₃ buffer, wt. % | Ave. foam stability (s) at 250° C. |
|---|---|---|---|
| 2:1 $C_{14}$-$C_{16}$ AOS/dodecene mixed dimer Na salt | 0.5 | 0.5 | 48 |
| 2:1 $C_{14}$-$C_{16}$ AOS/octene mixed dimer Na salt | 0.5 | 0.5 | 43 |

TABLE 6

Results from Foam Test Method 3

| Surfactant | Surfactant solids, wt. % | Ave. foam stability (s) at 250° C. |
|---|---|---|
| $C_{14}$-$C_{16}$ AOS dimer Na salt (control) | 0.5 | 56 |
| 2:1 $C_{14}$-$C_{16}$ AOS/hexadecene mixed dimer Na salt | 0.5 | 94 |
| 3:1 $C_{14}$-$C_{16}$ AOS/hexadecene mixed dimer Na salt | 0.5 | 103 |
| 3:2 $C_{14}$-$C_{16}$ AOS/hexadecene mixed dimer Na salt | 0.5 | 109 |
| 2:1 $C_{14}$-$C_{16}$ AOS/oleyl alcohol mixed oligomer Na salt | 0.5 | 93 |

TABLE 7

Results from Foam Test Method 4

| Surfactant | Surfactant solids, wt. % | Ave. foam stability at 250° C. (s) |
|---|---|---|
| $C_{14}$-$C_{16}$ AOS dimer Na salt (control) | 0.5 | 73 |
| 2:1 $C_{14}$-$C_{16}$ AOS/hexadecene mixed dimer Na salt | 0.5 | 158 |
| 2:1 $C_{14}$-$C_{16}$ AOS/oleyl alcohol mixed oligomer Na salt | 0.5 | 197 |

The preceding examples are meant only as illustrations; the following claims define the invention.

We claim:

1. A mixed dimer composition comprising a monosulfonated cross-dimer, or a salt thereof, of:
   (a) an alpha-olefin sulfonic acid (AOS acid); and
   (b) an unsulfonated olefin, an unsulfonated olefin precursor, or a functionalized olefin.

2. The composition of claim 1 further comprising an AOS dimer acid or a salt thereof.

3. The composition of claim 1 wherein the AOS acid is a $C_4$-$C_{50}$ AOS acid.

4. The composition of claim 1 wherein the unsulfonated olefin is a $C_3$-$C_{50}$ alpha-olefin or a $C_4$-$C_{50}$ internal olefin.

5. The composition of claim 1 wherein the unsulfonated olefin precursor is selected from the group consisting of saturated aliphatic $C_3$-$C_{50}$ alcohols and saturated aliphatic $C_3$-$C_{50}$ alkyl halides.

6. The composition of claim 1 wherein the functionalized olefin is an unsaturated fatty acid or an unsaturated fatty alcohol.

7. The composition of claim 1 wherein the monosulfonated cross-dimer has a general structure selected from the group consisting of:

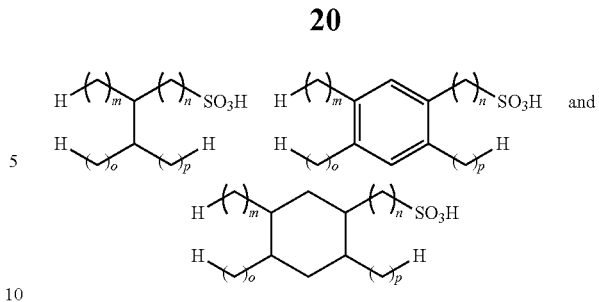

wherein m+n=3 to 49 and o+p=2 to 49 in the acyclic structure, and m+n=1 to 47 and o+p=0 to 47 in the cyclic structures, provided that the cross-dimer has at least 10 carbons.

8. The composition of claim 1 wherein the monosulfonated cross-dimer has a general structure selected from the group consisting of:

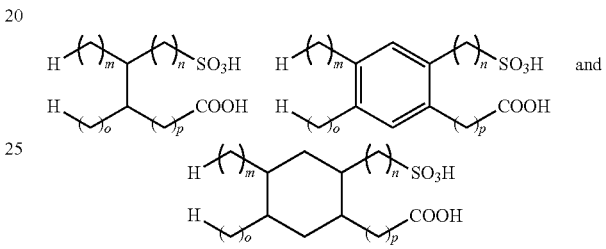

wherein m+n=3 to 49 and o+p=2 to 48 in the acyclic structure, and m+n=1 to 47 and o+p=0 to 46 in the cyclic structures, provided that the cross-dimer has at least 10 carbons.

9. A foam useful for oilfield or high-temperature applications, comprising (a) water; (b) a gas comprising steam, air, nitrogen, carbon dioxide, natural gas, or a mixture thereof; and (c) a surfactant comprising the composition of claim 1.

10. A mixed oligomer composition comprising a mono- or polysulfonated cross-oligomer, or a salt thereof, of:
    (a) an alpha-olefin sulfonic acid (AOS acid); and
    (b) an unsulfonated diolefin or an unsulfonated diolefin precursor.

11. The composition of claim 10 wherein the AOS acid is a $C_4$-$C_{50}$ AOS acid.

12. The composition of claim 10 wherein the unsulfonated diolefin is a $C_5$-$C_{50}$ linear or branched alpha- or internal diolefin.

13. The composition of claim 10 wherein the unsulfonated diolefin precursor is selected from the group consisting of $C_5$-$C_{50}$ diols, $C_5$-$C_{50}$ dihalides, monounsaturated aliphatic $C_5$-$C_{50}$ alcohols, and monounsaturated aliphatic $C_5$-$C_{50}$ alkyl halides.

14. The composition of claim 10 wherein the polysulfonated cross-oligomer has the general structure:

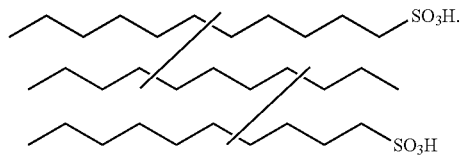

wherein any of the crosslinked fatty chains can have from 5 to 50 carbons.

15. The composition of claim 10 wherein the polysulfonated cross-oligomer has the general structure:

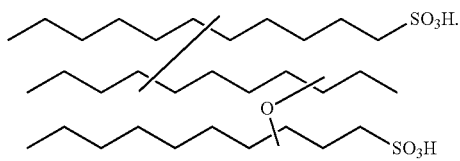

wherein any of the crosslinked fatty chains can have from 5 to 50 carbons.

16. A foam useful for oilfield or high-temperature applications, comprising (a) water; (b) a gas comprising steam, air, nitrogen, carbon dioxide, natural gas, or a mixture thereof; and (c) a surfactant comprising the composition of claim 10.

17. A method which comprises:
(a) sulfonating an alpha-olefin to produce a mixture comprising an alpha-olefin sulfonic acid and sulfur dioxide;
(b) heating the mixture from step (a) with
 (i) an unsulfonated olefin, an unsulfonated olefin precursor, or a functionalized olefin; or
 (ii) an unsulfonated diolefin or an unsulfonated diolefin precursor;
 in a reactor at a temperature within the range of 110° C. to 200° C. to produce a mixed dimer or mixed oligomer composition.

18. The method of claim 17 wherein sulfur dioxide is removed from the mixture produced in step (a) by digesting, vacuum stripping, gas purging, solvent-assisted stripping, heating, or a combination thereof.

19. A method which comprises:
(a) injecting into a subterranean reservoir formation, said formation comprising at least one injection well and at least one production well,
 (i) a mixed dimer composition comprising a monosulfonated cross-dimer, or a salt thereof, of:
  (A) an alpha-olefin sulfonic acid (AOS acid); and
  (B) an unsulfonated olefin, an unsulfonated olefin precursor, or a functionalized olefin; or
 (ii) a mixed oligomer composition comprising a mono- or polysulfonated cross-oligomer, or a salt thereof, of:
  (A) an alpha-olefin sulfonic acid (AOS acid); and
  (B) an unsulfonated diolefin or an unsulfonated diolefin precursor; and
(b) recovering oil from the production well.

20. The method of claim 19 wherein the method is a steam-assisted gravity drainage (SAGD) method in which (a) the formation comprises a horizontal SAGD well pair wherein the injection well is located above the production well; (b) a horizontal, vertical, or angled secondary well is created above the well pair; and (c) a surfactant solution comprising the mixed dimer composition or the mixed oligomer composition is introduced into the secondary well before, during, or after introducing steam into the injection well, whereby the surfactant solution drains from the secondary well into a steam chamber of the injection well and combines with rising steam to produce a steam foam in the injection well.

* * * * *